(12) United States Patent
Perkins et al.

(10) Patent No.: US 9,719,849 B2
(45) Date of Patent: Aug. 1, 2017

(54) OPTICAL COMPUTING DEVICES WITH MULTIPLE BANDPASS FILTERS

(71) Applicant: Halliburton Energy Services, Inc., Houston, TX (US)

(72) Inventors: David L. Perkins, The Woodlands, TX (US); Robert Paul Freese, Pittsboro, NC (US); Christopher Michael Jones, Houston, TX (US); Richard Neal Gardner, Raleigh, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 136 days.

(21) Appl. No.: 14/434,591

(22) PCT Filed: May 8, 2014

(86) PCT No.: PCT/US2014/037254
§ 371 (c)(1),
(2) Date: Apr. 9, 2015

(87) PCT Pub. No.: WO2015/171146
PCT Pub. Date: Nov. 12, 2015

(65) Prior Publication Data
US 2016/0273960 A1  Sep. 22, 2016

(51) Int. Cl.
*G01N 21/00* (2006.01)
*G01J 1/04* (2006.01)
(Continued)

(52) U.S. Cl.
CPC .............. *G01J 1/0488* (2013.01); *G01J 1/44* (2013.01); *G01N 21/31* (2013.01); *G01N 21/314* (2013.01);
(Continued)

(58) Field of Classification Search
CPC ........ G01N 21/31; G01N 21/85; G01N 21/17; G01N 21/274; G01N 2021/3174;
(Continued)

(56) References Cited

U.S. PATENT DOCUMENTS 6,011,652 A  1/2000  Cushing
6,529,276 B1  3/2003  Myrick
(Continued)

FOREIGN PATENT DOCUMENTS

WO  2012134796 A1  10/2012
WO  2015171146 A1  11/2015

OTHER PUBLICATIONS

International Search Report and Written Opinion for PCT/US2014/037254 dated Feb. 4, 2015.

*Primary Examiner* — Michael P Stafira
(74) *Attorney, Agent, or Firm* — McDermott Will & Emery LLP (57) ABSTRACT

An example optical computing device includes an integrated computational element (ICE) core arranged within an optical train that optically interacts with electromagnetic radiation and a substance, the ICE core being further configured to operate in a optical region of interest corresponding to a characteristic of the substance, a first bandpass filter arranged in the optical train and configured to transmit the electromagnetic radiation across a first wavelength zone within the optical region of interest, a second bandpass filter arranged in the optical train and configured to transmit the electromagnetic radiation across a second wavelength zone within the optical region of interest, and a detector configured to receive electromagnetic radiation that has optically interacted with the substance and the ICE core and configured to generate an output signal corresponding to the characteristic of the substance.

21 Claims, 3 Drawing Sheets

(51) Int. Cl.
*G01N 21/31* (2006.01)
*G02B 5/28* (2006.01)
*G02B 27/10* (2006.01)
*G02B 27/14* (2006.01)
*G01J 1/44* (2006.01)

(52) U.S. Cl.
CPC ........... *G02B 5/288* (2013.01); *G02B 27/106* (2013.01); *G02B 27/14* (2013.01); *G01N 2021/317* (2013.01)

(58) Field of Classification Search
CPC ........... G01N 21/65; G01N 2021/3137; G01N 21/27; G01N 21/954; G01N 21/75; G01N 21/35; G01N 21/359; G01N 21/47; G01N 21/64
See application file for complete search history.

(56) References Cited

U.S. PATENT DOCUMENTS

| | | | |
|---|---|---|---|
| 2009/0219539 A1* | 9/2009 | Myrick | G01N 21/4738 356/445 |
| 2013/0284895 A1* | 10/2013 | Freese | G02B 27/1006 250/208.2 |
| 2013/0286399 A1 | 10/2013 | Freese et al. | |

\* cited by examiner

OPTICAL COMPUTING DEVICES WITH MULTIPLE BANDPASS FILTERS

BACKGROUND

The present disclosure relates to optical computing devices and, more particularly, to using multiple bandpass filters in optical computing devices to improve sensitivity and detectability.

Optical computing devices, also commonly referred to as "opticoanalytical devices," can be used to analyze and monitor a sample substance in real time. Such optical computing devices will often employ a light source that emits electromagnetic radiation that reflects from or is transmitted through the sample and optically interacts with an optical processing element to determine quantitative and/or qualitative values of one or more physical or chemical properties of the substance being analyzed. The optical processing element may be, for example, an integrated computational element (ICE). One type of an ICE is an optical thin film interference device, also known as a multivariate optical element (MOE). Each ICE can be designed to operate over a continuum of wavelengths in the electromagnetic spectrum from the vacuum-UV to infrared (IR) ranges, or any sub-set of that region. Electromagnetic radiation that optically interacts with the sample substance is changed and processed by the ICE so as to be measured by a detector. The output of the detector can be correlated to a physical or chemical property of the substance being analyzed.

A traditional ICE (hereafter "ICE core") includes first and second pluralities of optical thin film layers consisting of various materials whose complex indices of refraction and size (e.g., thickness) varies between each layer. An ICE core design refers to the substrate, number and thickness of the respective layers of the ICE core, and the complex refractive indices of the layers. The complex refractive index includes both the real and imaginary components of the refractive index. The layers are strategically deposited and sized so as to selectively pass predetermined fractions of electromagnetic radiation at different wavelengths configured to substantially mimic a regression vector corresponding to a particular physical or chemical property of interest of a substance of interest. Accordingly, an ICE core design will exhibit a transmission function that is weighted with respect to wavelength. As a result, the output light intensity from the ICE core conveyed to the detector may be related to the physical or chemical property of interest for the substance.

Optical computing devices that employ ICE cores generally incorporate a single bandpass element or filter to restrict the optical spectrum to regions of interest. This bandpass filter is often a commercially available wide optical bandpass filter. Such bandpass filters are normally chosen to isolate the optical region defined by a single short pass wavelength and a single long pass wavelength. However, in some applications these bandpass filters may encompass many wavelength regions where there is little information, and thereby decreasing sensitivity, detectability, and signal-to-noise ratios (SNR) of the optical computing device.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to optical computing devices and, more particularly, to using multiple bandpass filters in optical computing devices to improve sensitivity and detectability.

The systems and methods disclosed herein use multiple bandpass filters within an optical train of an optical computing device in order to increase sensitivity, detectability, and signal-to-noise ratios of the optical computing device. In some embodiments, first and second bandpass filters may be employed, where the first bandpass filter is configured to transmit light across a first wavelength zone and the second bandpass filter is configured to transmit light in a second wavelength zone. As a result, the first and second bandpass filters may cooperatively operate by transmitting light in two different wavelength zones, while selectively reflecting or attenuating adjacent wavelength zones, including any wavelength regions that may interpose the first and second wavelength zones. Advantageously, the first and second bandpass filters may be configured to operate in conjunction with the design of an integrated computational element (ICE core) by selectively passing light in predetermined optical regions or wavelength zones for which the ICE core is designed to operate. As a result, wavelength zones that include information unrelated to the characteristic of interest may be eliminated or suppressed.

The methods and systems disclosed herein may prove advantageous in optimizing optical computing devices that employ optical processing elements (e.g., ICE cores) for use in the oil and gas industry, such as for monitoring and detecting oil/gas-related substances (e.g., hydrocarbons, drilling fluids, completion fluids, treatment fluids, etc.). It will be appreciated, however, that the optimized optical computing devices disclosed herein may equally be used in other technology fields including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "characteristic" or "characteristic of interest" refers to a chemical, mechanical, or physical property of a substance or a sample of the substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "substance," or variations thereof, refers to at least a portion of matter or material of interest to be tested or otherwise evaluated using the optical computing devices described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. In some cases, the substance may also refer to a solid material such as, but not limited to, rock formations, concrete, solid wellbore surfaces, pipes or flow lines, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optically interact," or variations thereof, refers to the reflection, transmission, scattering, diffraction, or absorption of electromagnetic radiation either on, through, or from an optical processing element (e.g., an integrated computational element) or a substance being analyzed with the help of the optical processing element. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an integrated computational element (ICE). The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art.

As indicated above, the present disclosure provides or otherwise describes improved optical computing devices that use optical processing elements, such as integrated computational elements (ICE cores). In operation, an ICE core is capable of distinguishing electromagnetic radiation related to a characteristic of interest of a substance from electromagnetic radiation related to other components of the substance.

Figure 1:
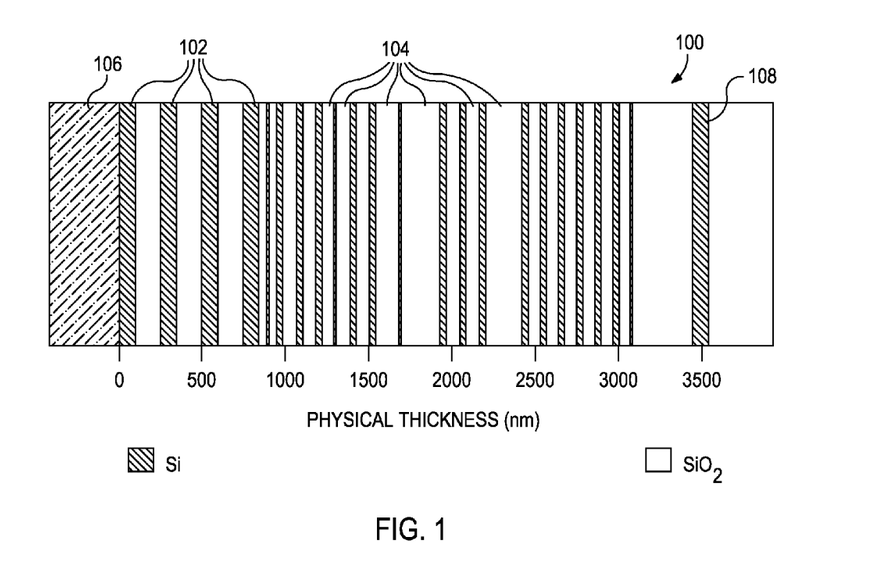
FIG. 1 illustrates an exemplary integrated computation element, according to one or more embodiments.

Referring to FIG. 1, illustrated is an ICE core 100. As illustrated, the ICE core 100 includes a plurality of alternating thin film layers shown as layers 102 and 104. The first layers 102 are made of a material that exhibits a high index of refraction, such as silicon (Si), and the second layers 104 are made of a material that exhibits a low index of refraction, such as quartz ($SiO_2$). Other examples of materials that might be used include, but are not limited to, niobia and niobium, germanium and germania, MgF, SiO, and other high and low index materials generally known in the art. The layers 102, 104 are strategically deposited on an optical substrate 106, such as BK-7 optical glass. In other embodiments, the substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the substrate 106 in FIG. 1), the ICE core 100 may include a layer 108 that is generally exposed to the environment of the device or installation. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the ICE core 100 depicted in FIG. 1 does not in fact represent any particular ICE core configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 will be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength are set to the regression weightings described with respect to a known equation, or data, or spectral signature. For instance, when electromagnetic radiation interacts with a substance, unique physical and chemical information about the substance is encoded in the electromagnetic radiation that is reflected from, transmitted through, or radiated from the substance. This information is often referred to as the spectral "fingerprint" of the substance. The ICE core 100 is configured to perform the dot product of the received electromagnetic radiation and the wavelength dependent transmission function of the ICE core 100. The wavelength dependent transmission function of the ICE core 100 is dependent on the substrate, the material complex indices of refraction of each layer, the number of layers 102, 104 and thickness of each layer 102, 104. As a result, the output light intensity of the ICE core 100 is related to the characteristic or analyte of interest.

As further explanation, accurately determining the regression vector of the characteristic of interest in the sample substance provides a means for an optical computing device to determine or otherwise calculate a concentration of said characteristic in the sample substance. The regression vector for each characteristic may be determined using standard procedures that will be familiar to one having ordinary skill in the art. For example, analyzing the spectrum of the sample substance may include determining a dot product of the regression vector for each characteristic of the sample substance being analyzed. As one of ordinary skill in art will recognize, a dot product of a vector is a scalar quantity (i.e., a real number). While the dot product value is believed to have no physical meaning by itself (e.g., it may return a positive or negative result of any magnitude), comparison of the dot product value of a sample substance with dot product values obtained for known reference standards and plotted in a calibration curve may allow the sample substance dot product value to be correlated with a concentration or value of a characteristic, thereby allowing unknown sample substances to be accurately analyzed.

To determine the dot product, one multiples the regression coefficient of the regression vector at a given wavelength by the spectral intensity at the same wavelength. This process is repeated for all wavelengths analyzed, and the products are summed over the entire wavelength range to yield the dot product. Those skilled in the art will recognize that two or more characteristics may be determined from a single spectrum of the sample substance by applying a corresponding regression vector for each characteristic.

In practice, it is possible to derive information from electromagnetic radiation interacting with a sample substance by, for example, separating the electromagnetic radiation from several samples into wavelength bands and performing a multiple linear regression of the band intensity against a characteristic of interest determined by another measurement technique for each sample substance. The measured characteristic may be expressed and modeled by multiple linear regression techniques that will be familiar to one having ordinary skill in the art. Specifically, if y is the measured value of the concentration or characteristic, y may be expressed as in Equation 1:

$$y = a_0 + a_1 w_1 + a_2 w_2 + a_3 w_3 + a_4 w_4 + \qquad (1)$$

where each 'a' is a constant determined by the regression analysis and each 'w' is the light intensity for each wavelength band. Depending on the circumstances, the estimate obtained from Equation (1) may be inaccurate, for example, due to the presence of other characteristics within the sample substance that may affect the intensity of the wavelength bands. A more accurate estimate may be obtained by expressing the electromagnetic radiation in terms of its principal components.

To obtain the principal components, spectroscopic data is collected for a variety of similar sample substances using the same type of electromagnetic radiation. For example, following exposure to each sample substance, the electromagnetic radiation may be collected and the spectral intensity at each wavelength may be measured for each sample substance. This data may then be pooled and subjected to a linear-algebraic process known as singular value decomposition (SVD) in order to determine the principal components. Use of SVD in principal component analysis will be well understood by one having ordinary skill in the art. Briefly, however, principal component analysis is a dimension reduction technique that takes 'm' spectra with 'n' independent variables and constructs a new set of eigenvectors that are linear combinations of the original variables. The eigenvectors may be considered a new set of plotting axes. The primary axis, termed the first principal component, is the vector that describes most of the data variability. Subsequent principal components describe successively less sample variability, until the higher order principal components essentially describe only spectral noise.

Typically, the principal components are determined as normalized vectors. Thus, each component of an electromagnetic radiation sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. Normalization determines values for a component at each wavelength so that the component maintains its shape and the length of the principal component vector is equal to one. Thus, each normalized component vector has a shape and a magnitude so that the components may be used as the basic building blocks of any electromagnetic radiation sample having those principal components. Accordingly, each electromagnetic radiation sample may be described by a combination of the normalized principal components multiplied by the appropriate scalar multipliers, as set forth in Equation (2):

$$x_1 z_1 + x_2 z_2 + \ldots + x_n z_n \qquad (2)$$

The scalar multipliers $x_n$ may be considered the "magnitudes" of the principal components in a given electromagnetic radiation sample when the principal components are understood to have a standardized magnitude as provided by normalization.

Because the principal components are orthogonal, they may be used in a relatively straightforward mathematical procedure to decompose an electromagnetic radiation sample into the component magnitudes, which may accurately describe the data in the original electromagnetic radiation sample. Since the original electromagnetic radiation sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Moreover, because the principal components are orthogonal to each other, the dot product of any principal component with any other principal component is zero. Physically, this means that the components do not spectrally interfere with each other. If data is altered to change the magnitude of one component in the original electromagnetic radiation signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the electromagnetic radiation samples. Thus, in a mathematical sense, the principal components are components of the original electromagnetic radiation that do not interfere with each other and that represent the most compact description of the spectral signal. Physically, each principal component is an electromagnetic radiation signal that forms a part of the original electromagnetic radiation signal. Each principal component has a shape over some wavelength range within the original wavelength range. Summing the principal components may produce the original signal, provided each component has the proper magnitude, whether positive or negative.

The principal components may comprise a compression of the information carried by the total light signal. In a physical sense, the shape and wavelength range of the principal components describe what information is in the total electromagnetic radiation signal, and the magnitude of each component describes how much of that information is present. If several electromagnetic radiation samples contain the same types of information, but in differing amounts, then a single set of principal components may be used to describe (except for noise) each electromagnetic radiation sample by applying appropriate magnitudes to the components. The principal components may be used to provide an estimate of the characteristic of the sample substance based upon the information carried by the electromagnetic radiation that has interacted with that sample substance. Differences observed in spectra of sample substances having varying quantities of an analyte or values of a characteristic may be described as differences in the magnitudes of the principal components. Thus, the concentration of the characteristic may be expressed by the principal components according to Equation (3) in the case where four principal components are used:

$$y = a_0 + a_1 x_1 + a_2 x_2 + a_3 x_3 + a_4 x_4 + \quad (3)$$

where 'y' is a concentration or value of a characteristic, each 'a' is a constant determined by the regression analysis, and $x_1$, $x_2$, $x_3$ and $x_4$ are the first, second, third, and fourth principal component magnitudes, respectively. Equation (3) may be referred to as a regression vector. The regression vector may be used to provide an estimate for the concentration or value of the characteristic for an unknown sample.

Regression vector calculations may be performed by computer, based on spectrograph measurements of electromagnetic radiation by wavelength. The spectrograph system spreads the electromagnetic radiation into its spectrum and measures the spectral intensity at each wavelength over the wavelength range. Using Equation (3), the computer may read the intensity data and decompose the electromagnetic radiation sample into the principal component magnitudes $x_n$ by determining the dot product of the total signal with each component. The component magnitudes are then applied to the regression equation to determine a concentration or value of the characteristic.

To simplify the foregoing procedure, however, the regression vector may be converted to a form that is a function of wavelength so that only one dot product is determined. Each normalized principal component vector $z_n$ has a value over all or part of the total wavelength range. If each wavelength value of each component vector is multiplied by the regression constant and corresponding to the component vector, and if the resulting weighted principal components are summed by wavelength, the regression vector takes the form of Equation (4):

$$y = a_0 + b_1 u_1 + b_2 u_2 + \ldots + b_n u_n \quad (4)$$

where $a_0$ is the first regression constant from Equation (3), $b_n$ is the sum of the multiple of each regression constant $a_n$ from Equation (3) and the value of its respective normalized regression vector at wavelength 'n', and $u_n$ is the intensity of the electromagnetic radiation at wavelength 'n'. Thus, the new constants define a vector in wavelength space that directly describes a concentration or characteristic of a sample substance. The regression vector in the form of Equation (4) represents the dot product of an electromagnetic radiation sample with this vector.

Normalization of the principal components provides the components with an arbitrary value for use during the regression analysis. Accordingly, it is very unlikely that the dot product value produced by the regression vector will be equal to the actual concentration or characteristic value of a sample substance being analyzed. The dot product result is, however, related (e.g., proportional or having a logarithmic or exponential relationship) to the concentration or characteristic value. As discussed above, the relationship may be determined by measuring one or more known calibration samples by conventional means and comparing the result to the dot product value of the regression vector. Thereafter, the dot product result can be compared to the value obtained from the calibration standards in order to determine the concentration or characteristic of an unknown sample being analyzed.

Figure 2:
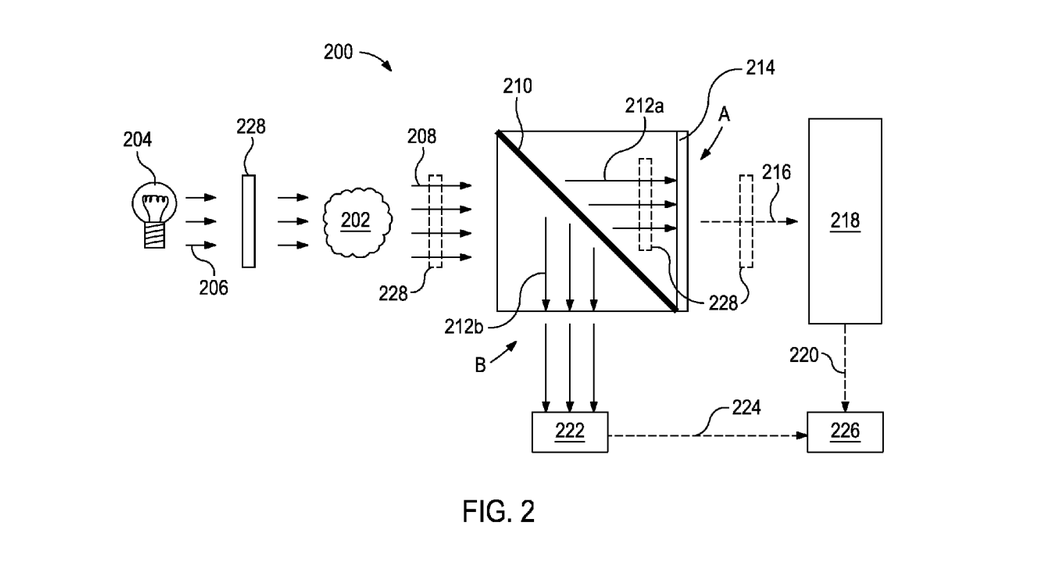
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of a substance 202 from other electromagnetic radiation. As shown in FIG. 2, an electromagnetic radiation source 204 may emit or otherwise generate electromagnetic radiation 206, where the electromagnetic radiation 206 is any type as described herein. In some embodiments, the electromagnetic radiation source 204 is a light bulb, a light emitting diode (LED), a laser, a blackbody, a photonic crystal, an X-Ray source, a supercontinuum source, combinations thereof, or the like. The electromagnetic radiation 206 is directed toward the substance 202, which contains an analyte of interest (e.g., a characteristic of the substance 202) desired to be determined. The electromagnetic radiation 206 optically interacts with the substance 202 and produces optically interacted radiation 208 (e.g., sample-interacted light), some of which may be electromagnetic radiation corresponding to the characteristic or analyte of interest and some of which may be background electromagnetic radiation corresponding to other components or characteristics of the substance 202.

While FIG. 2 shows the electromagnetic radiation 206 as passing through the substance 202, other embodiments of the device 200 may reflect the electromagnetic radiation 206 off the substance 202, such as may be required when the substance 202 is translucent, opaque, or solid, and equally produce the optically interacted radiation 208. Moreover, in some embodiments, the electromagnetic radiation source 204 may be omitted altogether and the required electromagnetic radiation may be derived from the substance 202 itself. For example, various substances naturally radiate electromagnetic radiation, such as a blackbody radiating substance that radiates electromagnetic radiation in the form of heat. In other embodiments, the substance 202 may be radioactive or chemo-luminescent and, therefore, radiate electromagnetic radiation. In yet other embodiments, the required electromagnetic radiation may be induced from the substance 202 by being acted upon mechanically, magnetically, electrically, combinations thereof, or the like.

The optically interacted radiation 208 may impinge upon the optical computing device 200, which may contain, for example, a beam splitter 210. The beam splitter 210 may be configured to split the optically interacted radiation 208 into a first beam of light 212a directed in a first or primary channel A and a second beam of light 212b directed in a second or reference channel B. As used herein, the term "channel" refers generally to an optical path, as known in the art. Within the first channel A, the first beam of light 212a is directed toward an ICE core 214, which may be substantially similar to the ICE core 100 described above with reference to FIG. 1. The ICE core 214 may be configured to produce modified electromagnetic radiation 216 corresponding to the characteristic or analyte of interest. In particular, the modified electromagnetic radiation 216 may include electromagnetic radiation that has optically interacted with the ICE core 214, whereby an approximation of the regression vector corresponding to the characteristic of interest is obtained.

Within the primary channel A, the modified electromagnetic radiation 216 is subsequently conveyed to a detector 218 for quantification. The detector 218 may be any device capable of detecting electromagnetic radiation, and may be generally characterized as an optical transducer. For example, the detector 218 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

The detector 218 may then produce an output signal 220 in the form of a voltage (or current) that corresponds to the particular characteristic of the substance 202. In at least one embodiment, the output signal 220 produced by the detector 218 and the concentration of the characteristic of the substance 202 may be directly proportional. In other embodiments, however, the relationship may correspond to a polynomial function, an exponential function, a logarithmic function, and/or a combination thereof.

The second beam of light 212b may be directed within the second channel B toward a second detector 222. The second detector 222 may be similar to the first detector 218 and capable of detecting electromagnetic radiation. The second detector 222 may be used to detect radiating deviations stemming from the electromagnetic radiation source 204. Undesirable radiating deviations can occur in the intensity of the light in the primary channel A due to a wide variety of reasons and causing various negative effects. These negative effects can be particularly detrimental for measurements taken over a period of time. Radiating deviations can include such things as, but not limited to, light intensity fluctuations of the electromagnetic radiation 206. It can also include interferent fluctuations, which may scatter or absorb light from the substance 202 as it moves through the interaction space as might occur if a foreign substance such as dirt or dust is entrained within the substance 202 or otherwise passes in front of the electromagnetic radiation source 204. Radiating deviations can also include a film of material build-up on the windows of an interrogation space, which has the effect of reducing the amount of light reaching the detector 222. Without proper compensation, such radiating deviations could result in false readings from the primary channel A, and the output signal 220 would no longer be primarily related to the characteristic of interest.

To correct or compensate for these types of undesirable effects, the second detector 222 may be configured to generate a compensating signal 224 generally indicative of the radiating deviations of the electromagnetic radiation source 204, and thereby normalize the output signal 220. Accordingly, the second channel B is often referred to as the "reference" channel. In some applications, the compensating signal 224 and the output signal 220 may be transmitted to or otherwise received by a signal processor 226 in communication with each detector 218, 222. The signal processor 226 may be configured to computationally combine the compensating signal 224 with the output signal 220 in order to normalize the output signal 220 in view of any radiating deviations as detected by the second detector 222. In some embodiments, computationally combining the output and compensating signals 220, 224 may entail computing a ratio of the two signals 220, 224, thereby essentially computing a ratio of the primary and reference channels A and B (e.g., A/B).

The signal processor 226 may also be configured to further process the output and compensating signals 220, 224 in order to provide additional characterization information about the substance 202 being analyzed. In some embodiments, the identification and concentration of each analyte in the substance 202 can be used to predict certain physical characteristics of the substance 202. For example, the bulk characteristics of a substance 202 can be estimated by using a combination of the properties conferred to the substance 202 by each analyte.

In some embodiments, the concentration of each analyte or the magnitude of each characteristic determined using the optical computing device 200 can be fed into an algorithm run by the signal processor 226. The algorithm may be configured to make predictions on how the characteristics of the substance 202 change if the concentrations of the analytes are changed relative to one another. In some embodiments, the algorithm produces an output that is readable by an operator who can consider the results and make proper adjustments or take appropriate action, if needed, based upon the output. The algorithm can be part of an artificial neural network configured to use the concentration of each detected analyte in order to evaluate the characteristic(s) of the substance 202 and, if desired, predict how to modify the substance 202 in order to alter its properties in a desired way.

In some embodiments, a bandpass filter 228 may be arranged in the optical train of the device 200. As used herein, the phrase "optical train" refers to the optical path that extends between the electromagnetic radiation source 204 and the first detector 218. In the illustrated embodiment, the bandpass filter 228 is depicted as being arranged within the optical train just after the electromagnetic radiation source 204 but before the substance 202. In other embodiments, however, the bandpass filter 228 (as shown in dashed) may equally be arranged following the substance 202, after passing through the beam splitter 210 and before the ICE core 214, or following the ICE core 214 but before reaching the first detector 218. In yet other embodiments, the bandpass filter 228 may be coupled to or otherwise replace the beam splitter 210, without departing from the scope of the disclosure. As will be appreciated, arranging the bandpass filter 228 in any of the aforementioned locations within the optical train will result in substantially the same output signal 220 as generated by the first detector 218.

The bandpass filter 228 may generally be designed to operate in transmission and thereby transmit light (e.g., electromagnetic radiation) in an optical region of interest or "passband" while simultaneously reflecting or otherwise attenuating optically adjacent wavelength zones. The bandpass filter 228 may be, for example, a top-hat filter or a notch filter. In other embodiments, the bandpass filters can be comprised of short and/or long pass filters that sufficiently transmit light in the optical region or regions of interest. In other embodiments, the bandpass filter 228 may be a dispersive spectrometer. In yet other embodiments, the bandpass filter 228 may be made up of pure or mixed compounds. Water, for example, constitutes a classic type of bandpass filter, but would require a cell to hold the liquid. Other solids, liquids, glasses (natural, doped or dyed), polymers, holographic elements, and gasses may also be used as the bandpass filter 228. Combinations of materials can also make up the bandpass filter 228, such as silicon and germanium.

Figure 3:
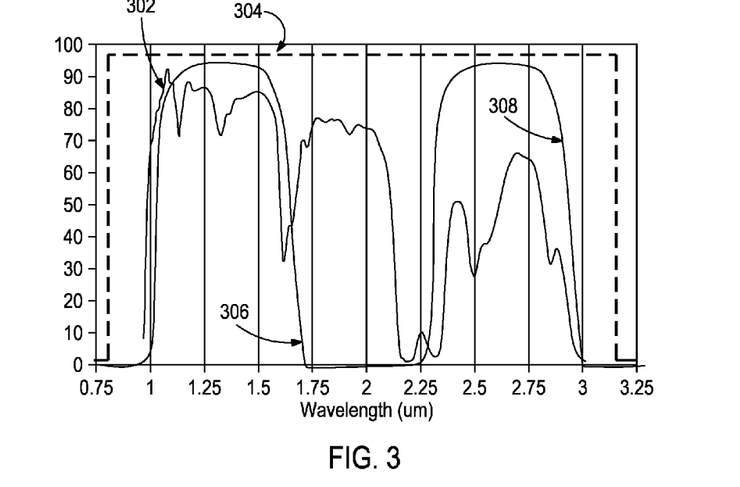
FIG. 3 depicts an exemplary transmission spectrum generated by the ICE core of FIG. 2.

The bandpass filter 228 may be designed to work in conjunction with the ICE core 214 by selectively passing light in a predetermined optical region for which the ICE core 214 is designed to operate. Referring to FIG. 3, for example, and with continued reference to FIG. 2, illustrated is an exemplary transmission spectrum 302 that may be generated by the ICE core 214 across an optical region of interest 304. In the illustrated embodiment, the optical region of interest 304 may extend generally between the 1.00 μm-3.00 μm wavelength range. In such an embodiment, the bandpass filter 228 may be configured to pass or transmit electromagnetic radiation between the 1.00 μm-3.00 μm wavelength range, but simultaneously reflect or otherwise attenuate adjacent wavelengths below 1.00 μm and above 3.00 μm. As a result, only the optical region of interest 304 (within the 1.00 μm-3.00 μm wavelength range) will ultimately be measured by the first detector 218.

In some embodiments, however, the 1.00 μm-3.00 μm wavelength range may include one or more wavelength bands or optical regions where there is little or no useful information for the particular design of the ICE core 214. For instance, the ICE core 214 may be designed and otherwise configured to detect methane, whose transmission function generally lies in the spectral regions between 1.00 μm-1.75 μm and 2.25 μm-3.00 μm. The optical region from 1.75 μm-2.25 μm, however, may be more related to an optical response for ethane, propane, or another analyte other than methane. As a result, the 1.75 μm-2.25 μm optical region would encompass useless information or "noise" that could have the effect of decreasing sensitivity, detectability, and signal-to-noise ratios (SNR) of the optical computing device 200 in detecting methane.

According to the present disclosure, the performance of an optical computing device may be improved by incorporating or otherwise employing at least two bandpass filters configured to limit the transmitted light to only the optical regions where the desired chemical or analyte information is encoded. For example, a first bandpass filter may be used to operate in a first wavelength zone 306, and a second bandpass filter may be used to operate in a second wavelength zone 308. As a result, the undesirable or useless spectral information for the application at hand may be substantially eliminated or suppressed, and thereby increase the sensitivity, detectability, and SNR of the optical computing device in the detection of the characteristic of interest.

Figure 4:
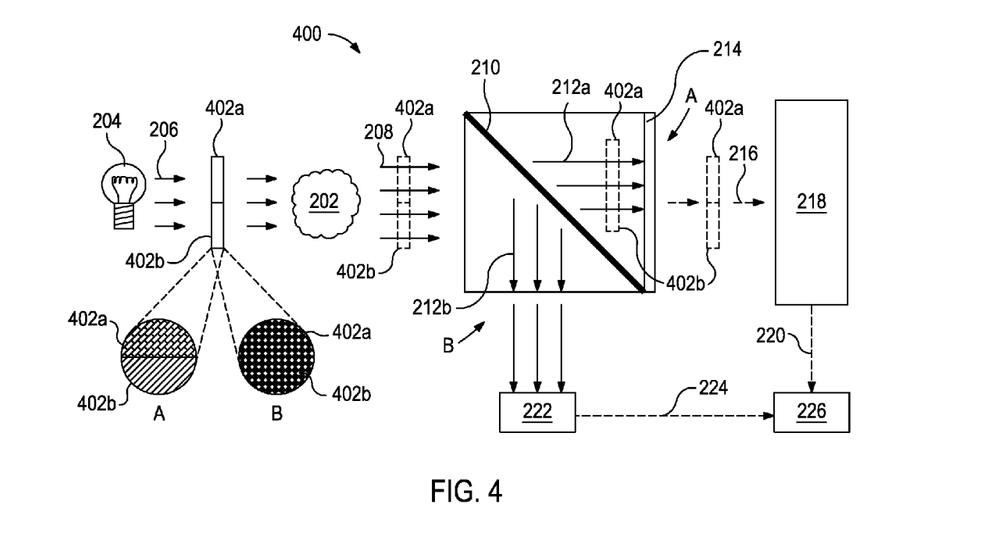
FIG. 4 illustrates another exemplary optical computing device, according to one or more embodiments.

Referring now to FIG. 4, with continued reference to FIGS. 2 and 3, illustrated is another exemplary optical computing device 400 that may be used to monitor the substance 202, according to one or more embodiments. The optical computing device (hereafter "the device 400") may be similar in some respects to the device 200 of FIG. 2 and therefore will be best understood with reference thereto, where like numerals represent like elements not described again in detail. As shown in FIG. 4, the electromagnetic radiation source 204 generates the electromagnetic radiation 206, which is directed toward the substance 202 in order to optically interact therewith and generate optically interacted radiation 208.

Again, while FIG. 4 shows the electromagnetic radiation 206 as passing through the substance 202 to produce the optically interacted radiation 208, the electromagnetic radiation 206 may equally be reflected off the substance 202 and equally obtain the optically interacted radiation 208. Moreover, in some embodiments, the electromagnetic radiation source 204 may be omitted from the device 200 and the required electromagnetic radiation may be derived from the substance 202 itself, as generally described above. In such embodiments, however, the optical train would extend from the substance 202 to the first detector 218.

The optically interacted radiation 208 is conveyed toward the beam splitter 210, which splits the optically interacted radiation 208 into the first and second beams of light 212a,b directed in the primary and reference channels A, B, respectively. The first beam of light 212a may optically interact with the ICE core 214, and the resulting modified electromagnetic radiation 216 corresponding to the characteristic or analyte of interest may subsequently be directed toward the first detector 218 for quantification. The second beam of light 212b is directed within the reference channel B toward the second detector 222 and, as described above, may be useful in detecting radiating deviations stemming from the electromagnetic radiation source 204. The output and compensating signals 220, 224 generated by the first and second detectors 218, 222 may then be conveyed to the signal processor 226, which computationally combines the signals 220, 224 in order to normalize the output signal 220 in view of any radiating deviations.

The device 400 may further include at least two bandpass filters, shown as a first bandpass filter 402a and a second bandpass filter 402b arranged in the optical train of the device 400. The first and second bandpass filters 402a,b may be similar to the bandpass filter 228 of FIG. 2. Accordingly, the first and second bandpass filters 402a,b may be, but are not limited to, top-hat filters, notch filters and dispersive spectrometers. In other embodiments, the bandpass filters can be comprised of short and/or long pass filters that sufficiently transmit light in the optical region or regions of interest. In yet other embodiments, the bandpass filters 402a,b may be made up of pure or mixed compounds, such as water, glasses (natural, doped, or dyed), polymers, holographic elements, gases, and a combination of materials (e.g., silicon and germanium). It will be appreciated that several of these examples may actually accomplish the two bandpass filters all in one. Water, for instance, exhibits several bandpass regions, and cuts out wavelength regions in between. One or both of the bandpass filters 402a,b may be constructed of a "cut-on" and/or "cut-off" filter set with light passing through both. Moreover, the bandpass filters 402a,b may be constructed using classic interference filter techniques, such as Fabry-Perot types.

In operation, the first bandpass filter 402a may be configured to transmit light across a first wavelength zone while simultaneously reflecting or otherwise attenuating adjacent wavelength zones. Similarly, the second bandpass filter 402b may be configured to transmit light in a second wavelength zone while simultaneously reflecting or otherwise attenuating adjacent wavelength zones. As a result, the first and second bandpass filters 402a,b may cooperatively operate by transmitting light in two different wavelength zones, while selectively reflecting or attenuating adjacent wavelength zones, including any wavelength regions that may interpose the first and second wavelength zones.

In order to allow the transmission of light in two different wavelength zones, while selectively attenuating adjacent wavelength zones, the first and second bandpass filters 402a,b may be arranged in various configurations, such as those depicted in exploded views "A" and "B" in FIG. 4. Views A and B represent frontal or normal views of two exemplary configurations of the first and second bandpass filters 402a,b. In view A, the first and second bandpass filters 402a,b are arranged in a conjoined semi-circular configuration, where the first bandpass filter 402a occupies about 50% of a filter interface and the second bandpass filter 402b occupies the remaining 50% of the filter interface. In the conjoined semi-circular configuration, the electromagnetic radiation 206 is able to impinge upon the filter interface and transmit through the first bandpass filter 402a across a first wavelength, while simultaneously being transmitted through the second bandpass filter 402b across a second wavelength zone. Wavelength zones falling outside of the first and second wavelength zones would be effectively reflected or attenuated.

In view B, the first and second bandpass filters 402a,b are arranged in a pattern such that the first bandpass filter 402a occupies about 50% of the filter interface and the second bandpass filter 402b occupies the remaining 50% of the filter interface. Similar to the configuration in view A, the electromagnetic radiation 206 is able to impinge upon the filter interface and transmit through the portions of filter interface associated with the first bandpass filter 402a across the first wavelength, while simultaneously being transmitted through the portions of filter interface associated with the second bandpass filter 402b across the second wavelength zone. Wavelength zones falling outside of the first and second wavelength zones would be effectively reflected or attenuated.

In the illustrated embodiment, the first and second bandpass filters 402a,b are depicted as being arranged together or otherwise in combination at a single location within the optical train. In such embodiments, the first and second bandpass filters 402a,b may be fabricated as a single optical bandpass device that may be selectively placed at various desired locations in the optical train. While depicted in FIG. 4 as being arranged within the optical train just after the electromagnetic radiation source 204 but before the substance 202, in other embodiments, the first and second bandpass filters 402a,b (as shown in dashed) may equally be arranged following the substance 202, after passing through the beam splitter 210 and before the ICE core 214, or following the ICE core 214 but before reaching the first detector 218. In yet other embodiments, the first and second bandpass filters 402a,b could be coupled to or otherwise replace the beam splitter 210, without departing from the scope of the disclosure.

In even further embodiments, the first and second bandpass filters 402a,b may be arranged separately at different locations within the optical train. In at least one embodiment, for instance, one of the first and second bandpass filters 402a,b may be coupled to or otherwise replace the beam splitter 210 while the other of the first and second bandpass filters 402a,b may be arranged at any other location within the optical train. In such an embodiment, the light paths extending to and from each bandpass filter 402a,b would have to be isolated or otherwise sufficiently separated from each other along much of the optical train so as to not attenuate desired wavelength zones. This may be possible by accurately collimating the light paths or through the use of optical light pipes or fibers. At some point following respective optical interaction with the first and second bandpass filters 402a,b, the light paths may be recombined for quantification in the first detector 218.

In yet other embodiments, at least one of the first and second bandpass filters 402a,b may be incorporated into or otherwise attached to the ICE core 214. More specifically, the ICE core 214 may be designed such that at least one of its layers 102, 104 (FIG. 1) may be one of the first and second bandpass filters 402a,b or otherwise form a terminal layer for the ICE core 214. In other embodiments, the first bandpass filter 402a, for example, may be coupled or otherwise attached to the exposed side of the substrate 106 (FIG. 1) and the second bandpass filter 402b may be coupled or otherwise attached to the exposed side of the terminal layer 108 (FIG. 1).

As will be appreciated, arranging the first and second bandpass filters 402a,b in any of the aforementioned locations within the optical train will result in substantially the same output signal 220 as generated by the first detector 218. In some embodiments, the detector 218 may be a monolithic detector. In other embodiments, however, the detector 218 may be a split detector, where separate portions of the detector 218 are configured to receive corresponding separate signals derived from the first and second bandpass filters 402a,b, respectively. The split detector may then be configured to computationally combine the separate signals derived from the first and second bandpass filters 402a,b in order to obtain the output signal 220.

More particularly, and with reference again to FIG. 3, the first and second bandpass filters 402a,b may advantageously be designed to work in conjunction with the ICE core 214 by selectively passing light in predetermined optical regions or wavelength zones for which the ICE core 214 is designed to operate. For instance, the ICE core 214 may be designed and otherwise configured to detect an analyte or characteristic whose spectral output generally lies in the optical region of interest 304 encompassing spectral regions between 1.00 µm-1.75 µm and 2.25 µm-3.00 µm. The wavelength zone that extends generally between 1.75 µm-2.25 µm, however, may generally include information that is not related to the characteristic of interest, and may therefore be characterized as unwanted noise.

In at least one embodiment, the first bandpass filter 402a may be configured to pass electromagnetic radiation over the first wavelength zone 306, which extends generally between 1.00 µm-1.75 µm, and the second bandpass filter 402b may be configured to pass electromagnetic radiation over the second wavelength zone 308, which extends generally between 2.25 µm-3.00 µm. As a result, the first and second bandpass filters 402a,b may be configured to pass or transmit electromagnetic radiation only within the first and second wavelength zones 306, 308 (i.e., between the 1.00 µm-1.75 µm and 2.25 µm-3.00 µm optical regions), respectively, but simultaneously reflect or otherwise attenuate adjacent wavelength regions below 1.00 µm, above 3.00 µm, and between 1.75 µm-2.25 µm. Upon being multiplied by the first detector 218, the undesirable 1.75 µm-2.25 µm wavelength zone incorporating information that is not relevant or of interest may, therefore, be cut out. Accordingly, the combined first and second bandpass filters 402a,b may be able to achieve corresponding passbands ranging between 1.00 µm-1.75 µm and between 2.25 µm-3.00 µm, and thereby eliminate the undesirable 1.75 µm-2.25 µm wavelength zone where there is relatively no useful information for the characteristic of interest but instead only detrimental and/or interferent optical signals.

It will be appreciated that the preceding example is provided for illustrative purposes only and, therefore, should not be considered as limiting to the present disclosure. For instance, the first and second wavelength zones of the first and second bandpass filters 402a,b, respectively, may be any wavelength zone of any size within the vacuum-UV to infrared (IR) ranges, or any sub-set of that region. In some embodiments, portions of the first and second wavelength zones may spectrally overlap.

Moreover, while the device 400 is depicted as employing two bandpass filters 402a and 402b, embodiments are also contemplated herein that employ more than two bandpass filters in order to selectively transmit light in desired spectral regions corresponding to the design of an ICE core, without departing from the scope of the disclosure. For instance, in at least one embodiment, the device 400 may include a third bandpass filter (not shown) configured to transmit light in a third wavelength zone falling within the optical region of interest 304 in which the ICE core 214 is designed to operate. The third bandpass filter may be coupled with the first and second bandpass filters 402a,b or otherwise arranged separately therefrom within the optical train.

Figure 5:
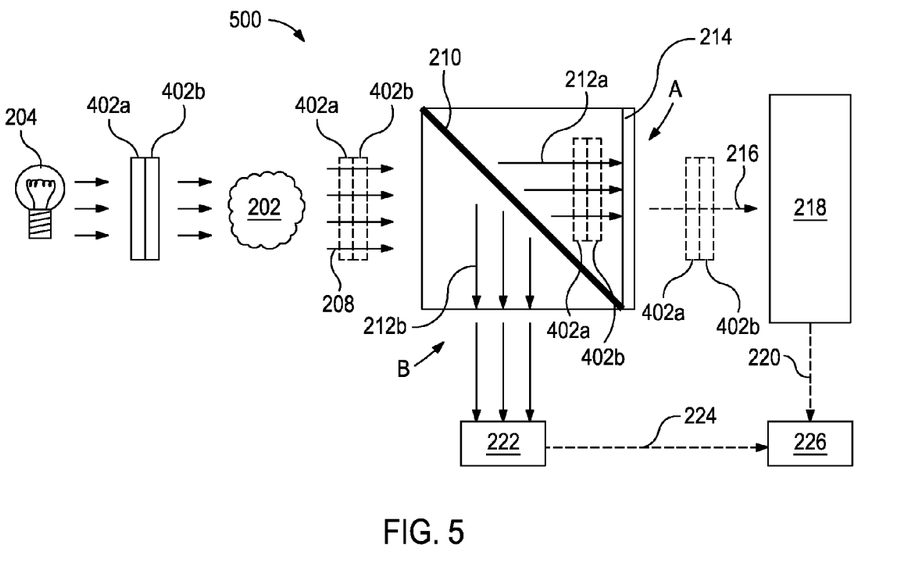
FIG. 5 illustrates another exemplary optical computing device, according to one or more embodiments.

Referring now to FIG. 5, with continued reference to FIGS. 3 and 4, illustrated is another exemplary optical computing device 500 that may be used to monitor the substance 202, according to one or more embodiments. The optical computing device (hereafter "the device 500") may be substantially similar to the device 400 of FIG. 2 and therefore will be best understood with reference thereto, where like numerals represent like elements not described again. Whereas in FIG. 4 the first and second bandpass filters 402a,b are depicted as being in a generally parallel relationship within the optical train, the first and second bandpass filters 402a,b are depicted in FIG. 5 in a series relationship within the optical train.

As with the device 400, the first and second bandpass filters 402a,b may be used to work in conjunction with the ICE core 214 by selectively passing electromagnetic radiation in predetermined optical regions or wavelength zones for which the ICE core 214 is designed to operate, while simultaneously blocking electromagnetic radiation across wavelength zones that do not include information related to the characteristic of interest. In the illustrated embodiment, the first bandpass filter 402a may be configured to pass electromagnetic radiation over one or more wavelength zones, and the second bandpass filter 402b may be configured to modify or otherwise optimize at least one of the one or more wavelength zones of the first bandpass filter 402a.

For instance, the first bandpass filter 402a may be made of water or a quarter wave stack interference filter (e.g., Fabry-Perot), which are both able to exhibit several different "pass" regions of transparency and thereby pass electromagnetic radiation over multiple more wavelength zones. The second bandpass filter 402b may be a notch filter, a cut-on filter, or a cut-off filter that may prove useful in eliminating or otherwise optimizing at least one of the multiple wavelength zones of the first bandpass filter 402a. As a result, the light transmitted through the first and second bandpass filters 402a,b may correspond more accurately to the characteristic of interest while simultaneously eliminating undesirable wavelength zones where there is relatively no useful information for the characteristic of interest but instead only detrimental and/or interferent optical signals.

Those skilled in the art will readily appreciate that using multiple bandpass filters in an optical computing device may also prove advantageous in the design of an ICE core. For instance, by utilizing multiple bandpass filters to restrict the ICE design space to more appropriate spectral regions, the design of an ICE core may become more tuned to finding the best designs for a given application. More particularly, by limiting the spectral region for operation, the time required to design an ICE core will not be spent on trying to produce a region when the ICE core spectral transmission is at or near zero, which is equivalent to isolating the undesired region using bandpass filters.

Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. An optical computing device that includes an integrated computational element (ICE) core arranged within an optical train and configured to optically interact with electromagnetic radiation and a substance, the substance being arranged in the optical train and the ICE core being further configured to operate in an optical region of interest corresponding to a characteristic of the substance, a first bandpass filter arranged in the optical train and configured to transmit the electromagnetic radiation across a first wavelength zone within the optical region of interest, a second bandpass filter arranged in the optical train and configured to transmit the electromagnetic radiation across a second wavelength zone within the optical region of interest, and a detector configured to receive electromagnetic radiation that has optically interacted with the substance and the ICE core and configured to generate an output signal corresponding to the characteristic of the substance.

B. A method that includes optically interacting electromagnetic radiation with a substance arranged within an optical train of an optical computing device, optically interacting an integrated computational element (ICE) core with the electromagnetic radiation and the substance, the ICE core being arranged within the optical train and configured to operate in an optical region of interest corresponding to a characteristic of the substance, receiving and transmitting the electromagnetic radiation across a first wavelength zone within the optical region of interest with a first bandpass filter arranged in the optical train, receiving and transmitting the electromagnetic radiation across a second wavelength zone within the optical region of interest with a second bandpass filter arranged in the optical train, receiving with a detector the electromagnetic radiation after having optically interacted with the substance and the ICE core, and generating an output signal corresponding to the characteristic of the substance with the detector.

Each of embodiments A and B may have one or more of the following additional elements in any combination: Element 1: further comprising an electromagnetic radiation source configured to emit the electromagnetic radiation into the optical train to optically interact with the substance and the ICE core. Element 2: wherein the electromagnetic radiation source is a source selected from the group consisting of a light bulb, a light emitting diode, a laser, a blackbody, a photonic crystal, an X-Ray source, a supercontinuum source, and any combination thereof. Element 3: wherein the substance is a material selected from the group consisting of air, nitrogen, carbon dioxide, argon, helium, methane, ethane, butane, hydrogen sulfide, a slurry, an emulsion, a powder, a mud, a glass, aqueous fluids, non-aqueous fluids, acids, surfactants, biocides, bleaches, corrosion inhibitors, foamers and foaming agents, breakers, scavengers, stabilizers, clarifiers, detergents, treatment fluids, fracturing fluids, formation fluids, rock formations, concrete, solid wellbore surfaces, pipes or flow lines, and solid surfaces of any wellbore tool or projectile. Element 4: further comprising a signal processor communicably coupled to the detector and configured to receive and process the output signal. Element 5: wherein the first and second bandpass filters are arranged in combination at a single location within the optical train. Element 6: wherein the single location within the optical train is at least one of after the electromagnetic radiation source but before the substance, after the substance, and after the ICE core but before the detector. Element 7: wherein the first and second bandpass filters are arranged separately at different locations within the optical train. Element 8: wherein the different locations within the optical train are at least one of after the electromagnetic radiation source but before the substance, after the substance, and after the ICE core but before the detector. Element 9: further including a beam splitter arranged in the optical train, wherein at least one of the first and second bandpass filters is coupled to the beam splitter. Element 10: wherein at least one of the first and second bandpass filters is coupled to the ICE core. Element 11: wherein the first and second bandpass filters are filters selected from the group consisting of a top-hat filter, a notch filter, a short-pass filter, a long-pass filter, a dispersive spectrometer, water, glasses, polymers, holographic elements, gases, and an interference filter. Element 12: wherein the optical region of interest corresponds to a spectral output of the characteristic of interest. Element 13: wherein at least a portion of the first and second wavelength zones spectrally overlap. Element 14: further comprising a third bandpass filter arranged in the optical train and configured to transmit light across a third wavelength zone within the optical region of interest.

Element 15: further comprising emitting the electromagnetic radiation into the optical train with an electromagnetic radiation source selected from the group consisting of a light bulb, a light emitting diode, a laser, a blackbody, a photonic crystal, an X-Ray source, a supercontinuum source, and any combination thereof. Element 16: further comprising receiving the output signal with a signal processor communicably coupled to the detector, and processing the output signal to quantify the characteristic of interest with the signal processor. Element 17: further comprising arranging the first and second bandpass filters in combination at a single location within the optical train. Element 18: further comprising arranging the first and second bandpass filters at separate locations within the optical train. Element 19: further comprising transmitting the electromagnetic radiation across a third wavelength zone within the optical region of interest with a third bandpass filter arranged in the optical train.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An optical computing device, comprising:
an integrated computational element (ICE) core arranged within an optical train and configured to optically interact with electromagnetic radiation and a substance, the substance being arranged in the optical train and the ICE core being further configured to operate in an optical region of interest corresponding to a characteristic of the substance;
a first bandpass filter arranged in the optical train and configured to transmit the electromagnetic radiation across a first wavelength zone within the optical region of interest;
a second bandpass filter arranged in the optical train and configured to transmit the electromagnetic radiation across a second wavelength zone within the optical region of interest, wherein the second wavelength zone is dissimilar to the first wavelength zone; and
a detector configured to receive electromagnetic radiation that has optically interacted with the substance and the ICE core and configured to generate an output signal corresponding to the characteristic of the substance.

2. The optical computing device of claim 1, further comprising an electromagnetic radiation source configured to emit the electromagnetic radiation into the optical train to optically interact with the substance and the ICE core.

3. The optical computing device of claim 2, wherein the electromagnetic radiation source is a source selected from the group consisting of a light bulb, a light emitting diode, a laser, a blackbody, a photonic crystal, an X-Ray source, a supercontinuum source, and any combination thereof.

4. The optical computing device of claim 1, wherein the substance is a material selected from the group consisting of air, nitrogen, carbon dioxide, argon, helium, methane, ethane, butane, hydrogen sulfide, a slurry, an emulsion, a powder, a mud, a glass, aqueous fluids, non-aqueous fluids, acids, surfactants, biocides, bleaches, corrosion inhibitors, foamers and foaming agents, breakers, scavengers, stabilizers, clarifiers, detergents, treatment fluids, fracturing fluids, formation fluids, rock formations, concrete, solid wellbore surfaces, pipes or flow lines, and solid surfaces of any wellbore tool or projectile.

5. The optical computing device of claim 1, further comprising a signal processor communicably coupled to the detector and configured to receive and process the output signal.

6. The optical computing device of claim 2, wherein the first and second bandpass filters are arranged in combination at a single location within the optical train.

7. The optical computing device of claim 6, wherein the single location within the optical train is at least one of after the electromagnetic radiation source but before the substance, after the substance, and after the ICE core but before the detector.

8. The optical computing device of claim 2, wherein the first and second bandpass filters are arranged separately at different locations within the optical train.

9. The optical computing device of claim 8, wherein the different locations within the optical train are at least one of after the electromagnetic radiation source but before the substance, after the substance, and after the ICE core but before the detector.

10. The optical computing device of claim 1, further including a beam splitter arranged in the optical train, wherein at least one of the first and second bandpass filters is coupled to the beam splitter.

11. The optical computing device of claim 1, wherein at least one of the first and second bandpass filters is coupled to the ICE core.

12. The optical computing device of claim 1, wherein the first and second bandpass filters are filters selected from the group consisting of a top-hat filter, a notch filter, a short-pass filter, a long-pass filter, a dispersive spectrometer, water, glasses, polymers, holographic elements, gases, and an interference filter.

13. The optical computing device of claim 1, wherein the optical region of interest corresponds to a spectral output of the characteristic of interest.

14. The optical computing device of claim 1, wherein at least a portion of the first and second wavelength zones spectrally overlap.

15. The optical computing device of claim 1, further comprising a third bandpass filter arranged in the optical train and configured to transmit light across a third wavelength zone within the optical region of interest.

16. A method, comprising:
optically interacting electromagnetic radiation with a substance arranged within an optical train of an optical computing device;
optically interacting an integrated computational element (ICE) core with the electromagnetic radiation and the substance, the ICE core being arranged within the optical train and configured to operate in an optical region of interest corresponding to a characteristic of the substance;
receiving and transmitting the electromagnetic radiation across a first wavelength zone within the optical region of interest with a first bandpass filter arranged in the optical train;
receiving and transmitting the electromagnetic radiation across a second wavelength zone within the optical region of interest and dissimilar to the first wavelength zone with a second bandpass filter arranged in the optical train;
receiving with a detector the electromagnetic radiation after having optically interacted with the substance and the ICE core; and
generating an output signal corresponding to the characteristic of the substance with the detector.

17. The method of claim 16, further comprising emitting the electromagnetic radiation into the optical train with an electromagnetic radiation source selected from the group consisting of a light bulb, a light emitting diode, a laser, a blackbody, a photonic crystal, an X-Ray source, a supercontinuum source, and any combination thereof.

18. The method of claim 16, further comprising:
   receiving the output signal with a signal processor communicably coupled to the detector; and
   processing the output signal to quantify the characteristic of interest with the signal processor.

19. The method of claim 16, further comprising arranging the first and second bandpass filters in combination at a single location within the optical train.

20. The method of claim 16, further comprising arranging the first and second bandpass filters at separate locations within the optical train.

21. The method of claim 16, further comprising transmitting the electromagnetic radiation across a third wavelength zone within the optical region of interest with a third bandpass filter arranged in the optical train.

\* \* \* \* \*